United States Patent
Aylsworth et al.

(10) Patent No.: US 7,007,692 B2
(45) Date of Patent: Mar. 7, 2006

(54) METHOD AND SYSTEM OF SENSING AIRFLOW AND DELIVERING THERAPEUTIC GAS TO A PATIENT

(75) Inventors: Alonzo C. Aylsworth, Wildwood, MO (US); Lawrence C. Spector, Austin, TX (US); Gregory R. Miller, Washington, MO (US)

(73) Assignee: AirMatrix Technologies, Inc., Wildwood, MO (US)

( * ) Notice: Subject to any disclaimer, the term of this patent is extended or adjusted under 35 U.S.C. 154(b) by 301 days.

(21) Appl. No.: 10/697,232

(22) Filed: Oct. 29, 2003

(65) Prior Publication Data
US 2005/0092321 A1 May 5, 2005

(51) Int. Cl.
*A61M 15/08* (2006.01)

(52) U.S. Cl. .......................... 128/203.22; 128/204.23; 128/204.26; 128/207.18

(58) Field of Classification Search ........... 128/203.22, 128/204.23, 204.26, 206.11, 207.18; 600/532, 600/535, 537, 538
See application file for complete search history.

(56) References Cited

U.S. PATENT DOCUMENTS

| | | | | |
|---|---|---|---|---|
| 2,007,287 A | * | 7/1935 | Shotton | 128/203.22 |
| 2,208,633 A | * | 7/1940 | Heidbrink | 128/203.28 |
| 3,566,862 A | * | 3/1971 | Schuh et al. | 601/44 |
| 4,054,133 A | * | 10/1977 | Myers | 128/204.26 |
| 4,278,110 A | * | 7/1981 | Price et al. | 137/805 |
| 4,428,372 A | | 1/1984 | Beysel et al. | |
| 4,457,303 A | * | 7/1984 | Durkan | 128/204.24 |
| 4,519,399 A | * | 5/1985 | Hori | 600/537 |
| 4,602,644 A | * | 7/1986 | DiBenedetto et al. | 600/538 |
| 4,706,664 A | | 11/1987 | Snook et al. | |
| 4,777,963 A | * | 10/1988 | McKenna | 600/537 |
| 4,832,014 A | * | 5/1989 | Perkins | 128/203.12 |
| 4,958,075 A | * | 9/1990 | Mace et al. | 250/343 |
| 4,989,599 A | * | 2/1991 | Carter | 128/207.18 |
| 5,005,571 A | * | 4/1991 | Dietz | 128/205.25 |
| 5,046,491 A | * | 9/1991 | Derrick | 128/200.24 |
| 5,069,222 A | * | 12/1991 | McDonald, Jr. | 600/537 |
| 5,099,836 A | * | 3/1992 | Rowland et al. | 128/204.23 |
| 5,134,995 A | * | 8/1992 | Gruenke et al. | 128/204.23 |
| 5,137,017 A | * | 8/1992 | Salter | 128/207.18 |
| 5,190,048 A | * | 3/1993 | Wilkinson | 600/537 |
| 5,199,423 A | | 4/1993 | Harral et al. | |
| 5,251,636 A | * | 10/1993 | Neuman | 600/537 |
| 5,279,304 A | * | 1/1994 | Einhorn et al. | 600/537 |
| 5,311,875 A | * | 5/1994 | Stasz | 600/537 |
| 5,335,656 A | * | 8/1994 | Bowe et al. | 128/207.18 |
| 5,413,111 A | * | 5/1995 | Wilkinson | 600/537 |
| 5,513,631 A | * | 5/1996 | McWilliams | 128/204.23 |
| 5,603,315 A | | 2/1997 | Sasso, Jr. | |
| 5,706,801 A | | 1/1998 | Remes et al. | |
| 5,755,224 A | | 5/1998 | Good et al. | |
| 5,803,066 A | * | 9/1998 | Rapoport et al. | 128/204.23 |

(Continued)

OTHER PUBLICATIONS

Salter Labs New Products Brochure, "New Product O₂XPRESS® Oxygen Conserver Device,".

(Continued)

*Primary Examiner*—Aaron J. Lewis
(74) *Attorney, Agent, or Firm*—Conley Rose, P.C.; Mark E. Scott

(57) ABSTRACT

Methods and related systems for individually sensing airflow in the breathing orifices of a patient, and preferentially delivering therapeutic gas to those breathing orifices based on the amount of airflow sensed.

46 Claims, 4 Drawing Sheets

U.S. PATENT DOCUMENTS

| | | | |
|---|---|---|---|
| 5,839,434 A | | 11/1998 | Enterline |
| 5,890,490 A | | 4/1999 | Aylsworth et al. |
| 6,029,664 A | | 2/2000 | Zdrojkowski et al. |
| 6,152,134 A | | 11/2000 | Webber et al. |
| 6,155,986 A | * | 12/2000 | Brydon et al. ............... 600/538 |
| 6,213,955 B1 | * | 4/2001 | Karakasoglu et al. ........ 600/529 |
| 6,379,312 B1 | * | 4/2002 | O'Toole ...................... 600/529 |
| 6,386,235 B1 | | 5/2002 | McCulloh et al. |
| 6,393,802 B1 | | 5/2002 | Bowser et al. |
| 6,394,088 B1 | | 5/2002 | Frye et al. |
| 6,446,630 B1 | | 9/2002 | Todd, Jr. |
| 6,565,517 B1 | * | 5/2003 | Rasmussen ................. 600/529 |
| 6,655,385 B1 | * | 12/2003 | Curti et al. ............. 128/207.18 |
| 6,805,126 B1 | * | 10/2004 | Dutkiewicz ............ 128/207.18 |
| 6,938,619 B1 | * | 9/2005 | Hickle ................... 128/207.18 |

OTHER PUBLICATIONS

Salter Labs Products Brochure, "ETCO$_2$ Sampling Cannulas,".

Hudson RCI Products Brochure, "Product Catalog, Cannulas, Masks, Tubing: Nasal Cannulas,".

"O$_2$N Demand® II Oxygen Conserver & Systems"; Victor Equipment Company Product Brochure No. 68-9902 (Jun. 2002).

"O$_2$N Demand® II Oxygen Conserver & Systems" operation instruction sheet available at least as early as the filing date of the current application.

* cited by examiner

METHOD AND SYSTEM OF SENSING AIRFLOW AND DELIVERING THERAPEUTIC GAS TO A PATIENT

CROSS-REFERENCE TO RELATED APPLICATIONS

None.

STATEMENT REGARDING FEDERALLY SPONSORED RESEARCH OR DEVELOPMENT

Not applicable.

BACKGROUND OF THE INVENTION

1. Field of the Invention

Embodiments of the invention are directed to preferentially delivering therapeutic gas to a patient. More particularly, the embodiments are directed to delivering therapeutic gas to one, a combination, or all of a patient's left naris, right naris and mouth selectively.

2. Background of the Invention

Patients with respiratory ailments may be required to breathe a therapeutic gas, such as oxygen. The therapeutic gas may be delivered to the patient from a therapeutic gas source by way of a nasal cannula.

Delivery of therapeutic gas to a patient may be continuous, or in a conserve mode. In continuous delivery, the therapeutic gas may be supplied at a constant flow throughout the patient's breathing cycle. A significant portion of the therapeutic gas provided in continuous delivery is wasted, i.e. the therapeutic gas delivered during exhalation of the patient is lost to atmosphere. In order to overcome the wastefulness of continuous delivery, related art devices may operate in conserve mode using a conserver system.

A conserver may be a device which senses a patient's inspiration, and delivers a bolus of therapeutic gas only during inspiration. By delivering therapeutic gas only during inspiration, the amount of therapeutic gas lost to atmosphere may be reduced. Conserver systems of the related art may sense a patient's inspiration at one naris and delivery the bolus of therapeutic gas to the other naris, such as through a bifurcated nasal cannula. Alternatively, conserver devices of the related art may sense a patient's inspiration at the nares generally, and delivery a bolus of therapeutic gas to the nares generally, such as through a non-bifurcated (single lumen) nasal cannula.

Sensing at one naris and delivering to a second naris may not work properly in all situations. If the patient has a blocked naris, e.g. because of congestion or some physical abnormality, either the sensing may not operate properly or the delivery of therapeutic gas may be to the blocked naris. Sensing and/or delivery may also fail to operate properly if the nasal cannula becomes dislodged, such as during sleep. Even if a nasal cannula stays properly on the patient and neither naris is blocked, delivering the patient's entire prescription of therapeutic gas through a single naris may cause nasal irritation.

When sensing inspiration by monitoring both nares simultaneously, congestion and/or abnormalities in the nares may cause the system to not sense properly. Moreover, when delivering therapeutic gas to the nares generally, such as through a single lumen cannula, congestion and/or physical abnormalities of the nares may affect the volume inhaled in each naris, wasting therapeutic gas in some cases and not providing sufficient therapeutic gas in other cases.

SUMMARY OF SOME OF THE PREFERRED EMBODIMENTS

The problems noted above may be solved in large part by a method and system of individually sensing airflow of the breathing orifices of a patient, and preferentially delivering therapeutic gas to those breathing orifices. One exemplary embodiment may be a method comprising sensing airflow of a first and second breathing orifice of a patient, delivering therapeutic gas to the first breathing orifice in proportion to the airflow of the first breathing orifice, and delivering therapeutic gas to the second breathing orifice in proportion to the airflow of the second breathing orifice.

The disclosed devices and methods comprise a combination of features and advantages which enable it to overcome the deficiencies of the prior art devices. The various characteristics described above, as well as other features, will be readily apparent to those skilled in the art upon reading the following detailed description, and by referring to the accompanying drawings.

BRIEF DESCRIPTION OF THE DRAWINGS

For a detailed description of the preferred embodiments of the invention, reference will now be made to the accompanying drawings in which.

NOTATION AND NOMENCLATURE

Certain terms are used throughout the following description and claims to refer to particular system components. This document does not intend to distinguish between components that differ in name but not function.

In the following discussion and in the claims, the terms "including" and "comprising" are used in an open-ended fashion, and thus should be interpreted to mean "including, but not limited to . . . ". Also, the term "couple" or "couples" is intended to mean either an indirect or direct electrical or mechanical connection. Thus, if a first device couples to a second device, that connection may be through a direct connection, or through an indirect connection via other devices and connections.

DETAILED DESCRIPTION OF THE PREFERRED EMBODIMENTS

Figure 1:
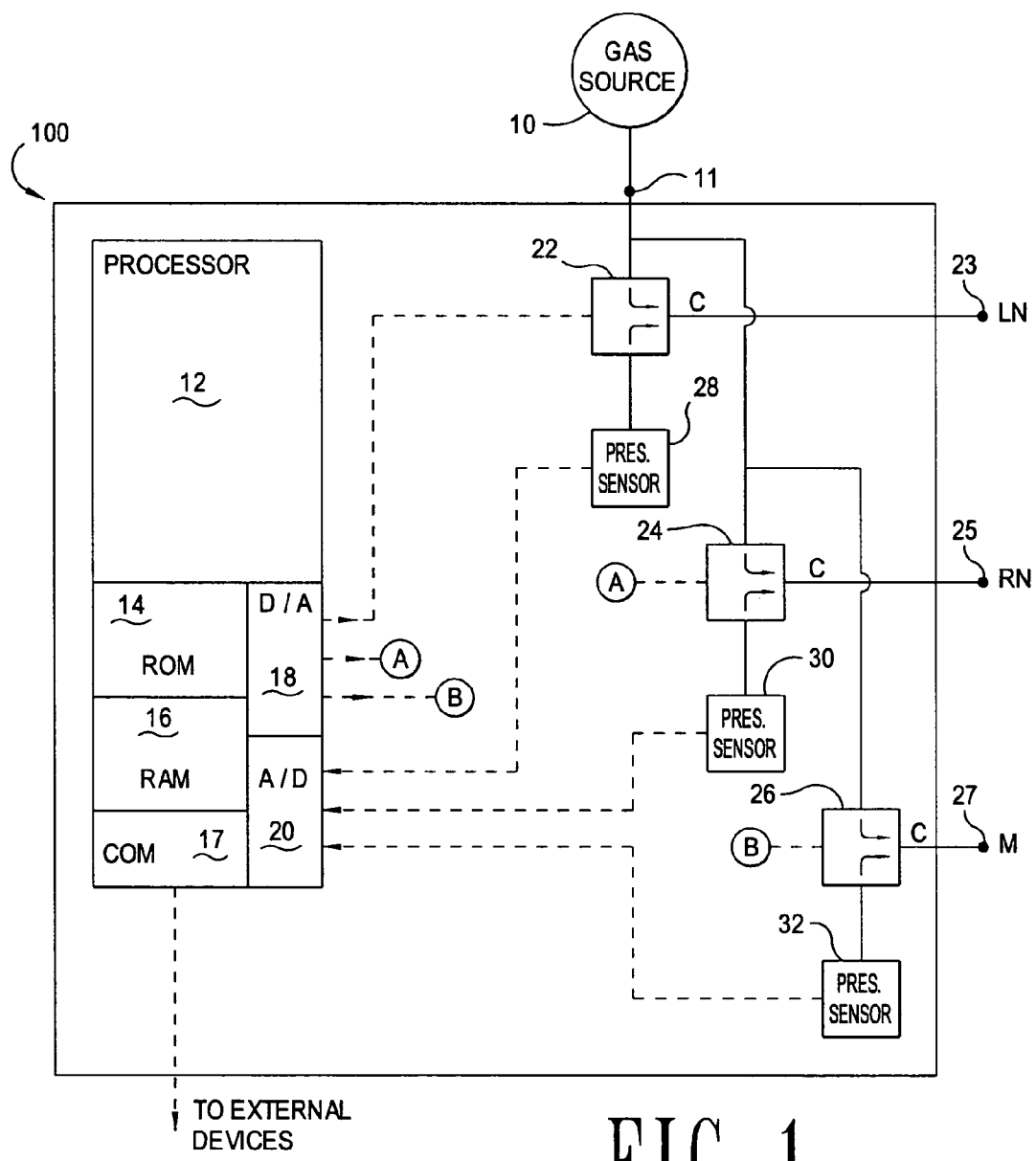
FIG. 1 illustrates a preferential delivery system in accordance with embodiments of the invention.

FIG. 1 illustrates a preferential delivery system 100 in accordance with at least some embodiments of the invention. The preferential delivery system 100 may be coupled to a therapeutic gas source 10 by way of a gas port 11. The therapeutic gas source 10 may be any suitable source of therapeutic gas, such as a portable cylinder, an oxygen concentration system or a permanent supply system as in a hospital. The selective delivery system also couples to a patient (not shown) by any of a variety of devices and systems by way of a variety of ports, such as narial ports 23, 25 and an oral port 27. For example, the preferential delivery system 100 may couple to a patient's nares by way of a nasal cannula. In accordance with embodiments of the invention, the preferential delivery system 100 monitors patient breathing and selectively delivers therapeutic gas to a left naris (LN), right naris (RN) and/or to the mouth (M) of the patient.

In accordance with at least some embodiments, the preferential delivery system 100 comprises both electrical components and mechanical components. In order to differentiate between electrical connections and mechanical connections, FIG. 1 (and the remaining figures) illustrate electrical connections between components with dashed lines, and fluid connections, e.g. tubing connections between devices, with solid lines. The preferential delivery system 100 in accordance with at least some embodiments of the invention comprises a processor 12. The processor 12 may be a microcontroller, and therefore the microcontroller may be integral with read-only memory (ROM) 14, random access memory (RAM) 16, a digital-to-analog converter (D/A) 18, and an analog-to-digital converter (A/D) 20. The processor 12 may further comprise communication logic 17, which allows the system 100 to communicate with external devices, e.g., to transfer stored data about a patient's breathing patterns. Although a microcontroller may be preferred because of the integrated components, in alternative embodiments the processor 12 may be implemented by a stand-alone central processing unit in combination with individual RAM, ROM, communication D/A and A/D devices.

The ROM 14 may store instructions executable by the processor 12. In particular, the ROM 14 may comprise a software program that implements the various embodiments of the invention discussed herein. The RAM 16 may be the working memory for the processor 12, where data may be temporarily stored and from which instructions may be executed. Processor 12 may couple to other devices within the preferential delivery system by way of A/D converter 20 and D/A converter 18.

Preferential delivery system 100 also comprises three-port valve 22, three-port valve 24, and three-port valve 26. In accordance with embodiments of the invention, each of these three-port valves may be a five-volt solenoid operated valve that selectively fluidly couples one of two ports to a common port (labeled as C in the drawings). Three-port valves 22, 24 and 26 may be Humprey Mini-Mizers having part No. D3061, such as may be available from the John Henry Foster Co., or equivalents. By selectively applying voltage on a digital output signal line coupled to the three-port valve 22, the processor 12 may be able to: couple gas from the gas source 10 to the common port and therefore to the exemplary left naris; and couple the pressure sensor 28 to the common port and therefore the exemplary left naris. Likewise, the three-port valve 24, under command of the processor 12, may: couple gas from the gas source 10 to the narial port 23 and therefore the exemplary right naris; and couple the pressure sensor 30 to the narial port 23 and therefore the exemplary right naris. Further still, three-port valve 26 under command of the processor 12, may: couple gas from the gas source 10 to the narial port 25 and therefore the patient's mouth; and couple the pressure sensor 32 to the narial port 25 and therefore the mouth. When the pressure sensors 28, 30 and 32 are coupled to the respective ports, the processor 12 may read (through corresponding A/D converter 20 input signal lines) pressures indicative of airflow by the patient through the respective breathing orifice. Thus, the processor 12 may be able to determine when the patient is inhaling, and how much of the air drawn by the patient flows through each of the monitored breathing orifices.

Consider a situation where the preferential delivery system 100 couples to the nares of the patient by way of a bifurcated nasal cannula. As the patient inhales, outlet ports in the nasal cannula proximate to the openings of each naris experience a drop in pressure. The drop in pressure may be sensed through the nasal cannula and associated hosing by each of the pressure sensors 28 and 30. Likewise, a sensing and delivery tube may be placed proximate to the patient's mouth, and thus pressure sensor 32 may detect an oral inspiration by the patient. In accordance with embodiments of the invention, the preferential delivery system 100 senses whether a patient has airflow through a monitored breathing orifice, and delivers therapeutic gas to the location or locations where the therapeutic gas may be inhaled by the patient.

Still considering the situation where the patient couples to the preferential delivery system 100 by way of a bifurcated nasal cannula and a separate sensing and delivery tube for the mouth, if there is no obstruction to inhalation in either of the nares or the mouth, therapeutic gas may be provided to any one or a combination of the nares and the mouth. Here, the preferential delivery system 100 may beneficially alternate the delivery site periodically so as to reduce discomfort associated with the therapeutic gas. Should the nasal cannula become partially dislodged, therapeutic gas may be provided only to the naris where the outlet port of the nasal cannula is still in operational relationship to the naris. Should the patient's nares become congested or blocked, therapeutic gas may be provided to the naris that is open.

The embodiments of the invention described above may work equally well in systems delivering a continuous flow of therapeutic gas, as well as systems operating in a conserve mode. In the continuous mode of operation, each of the three-port valves 22, 24 and 26 may couple therapeutic gas to their respective breathing orifice for extended periods of time, e.g. several respiratory cycles. Periodically, therapeutic gas delivery may cease and the preferential delivery system 100 may monitor the breathing pattern of the patient. That is, one or more of the three-port valves 22, 24 and 26 may change valve position, thus coupling pressure sensors to their respective breathing orifices and stopping therapeutic gas flow. If a monitored breath or breaths show that none of the possible breathing orifices are blocked, then the system 100 may simply switch back to the continuous mode of operation. If the preferential delivery system cannot detect an inhalation for any one of the breathing orifices, continuous flow mode may be resumed without providing therapeutic gas to the breathing orifice experiencing a problem.

In alternative embodiments, the preferential delivery system 100 may operate in a conserve mode, delivering a bolus of gas during each inhalation of the patient. Consider for purposes of explanation the left naris illustrated in FIG. 1, as well as its associated three-port valve 22 and pressure sensor 28. Prior to an inspiration, the three-port valve 22 may couple the pressure sensor to the common port of three-port valve 22 and therefore the left naris. As the patient starts an inhalation, as sensed by the pressure sensor 28 and read by processor 12, the three-port valve 22 changes valve position (as commanded by processors 12) and couples the therapeutic gas source 10 to the common port (and effectively blocking the pressure sensor from the common port). For a period of time, e.g. 100 mili-seconds, therapeutic gas may flow to the exemplary left naris. When the desired bolus volume has been delivered, possibly as a function of flow rate of the therapeutic gas and time, the processor 12 may command the three-port valve 22 to its original state, again fluidly coupling the pressure sensor 28 to the left naris. During exhalation, again sensed by pressure sensor 28, the three-port valve 22 remains in the valve position coupling the pressure sensor to the common port, and therefore no therapeutic gas is delivered. This exemplary process is equally applicable to three-port valve 24 and pressure sensor 30 in operational relationship to the right naris, as well as three-port valve 26 and pressure sensor 32 in operational relationship to the patient's mouth. Thus, in conserve mode, the preferential delivery system 100 may detect whether the nares and/or mouth are open to therapeutic gas flow with each inspiration. In the event an inspiration on any particular delivery path is not detected, indicating a blockage or other gas delivery problem (such as a dislodged cannula), the preferential delivery system 100 may refrain from providing therapeutic gas to that breathing orifice.

Figure 2A:
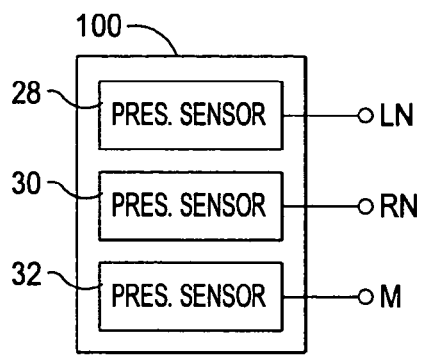
FIG. 2A illustrates, in shorthand notation, the system of FIG. 1.
Figure 2B:
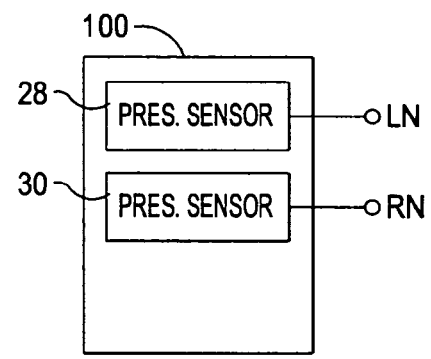
FIG. 2B illustrates an alternative embodiment of the system of FIG. 1.
Figure 2C:
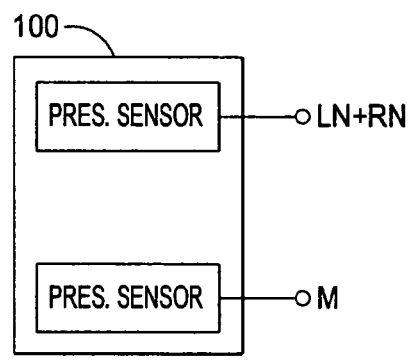
FIG. 2C illustrates yet another alternative embodiment of the system of FIG. 1.

FIG. 2A illustrates the preferential delivery system 100 of FIG. 1 in a shorthand notation, showing only pressure sensors 28, 30 and 32 coupled to the respective breathing orifices. FIG. 2B illustrates alternative embodiments of the invention monitoring and delivering therapeutic gas only to the nares of a patient. In the embodiments of FIG. 2B, if both the left naris and right naris are open to flow the preferential delivery system 100 may deliver therapeutic gas to either naris, to both nares, or in an alternating fashion. In the event that either the left or right naris become clogged or blocked, or if the sensing and delivery tubing (such as a nasal cannula) become dislodged, the preferential delivery system may provide therapeutic gas to the naris where airflow is sensed. FIG. 2C illustrates alternative embodiments of the invention where two pressure sensors are used, but in this case only one pressure sensor is associated with the nares, and the second pressure sensor is associated with the mouth. In the embodiments of FIG. 2C, a patient may utilize a single lumen cannula and a second sensing and delivery tube associated with the mouth. The preferential delivery system 100 may thus selectively provide therapeutic gas to the nares and/or to the mouth. In the event that either of the nares as a group or the mouth become blocked or otherwise unavailable for inspiration, the preferential delivery system 100 preferably provides therapeutic gas to the breathing orifice through which inhalation takes place.

Figure 3:
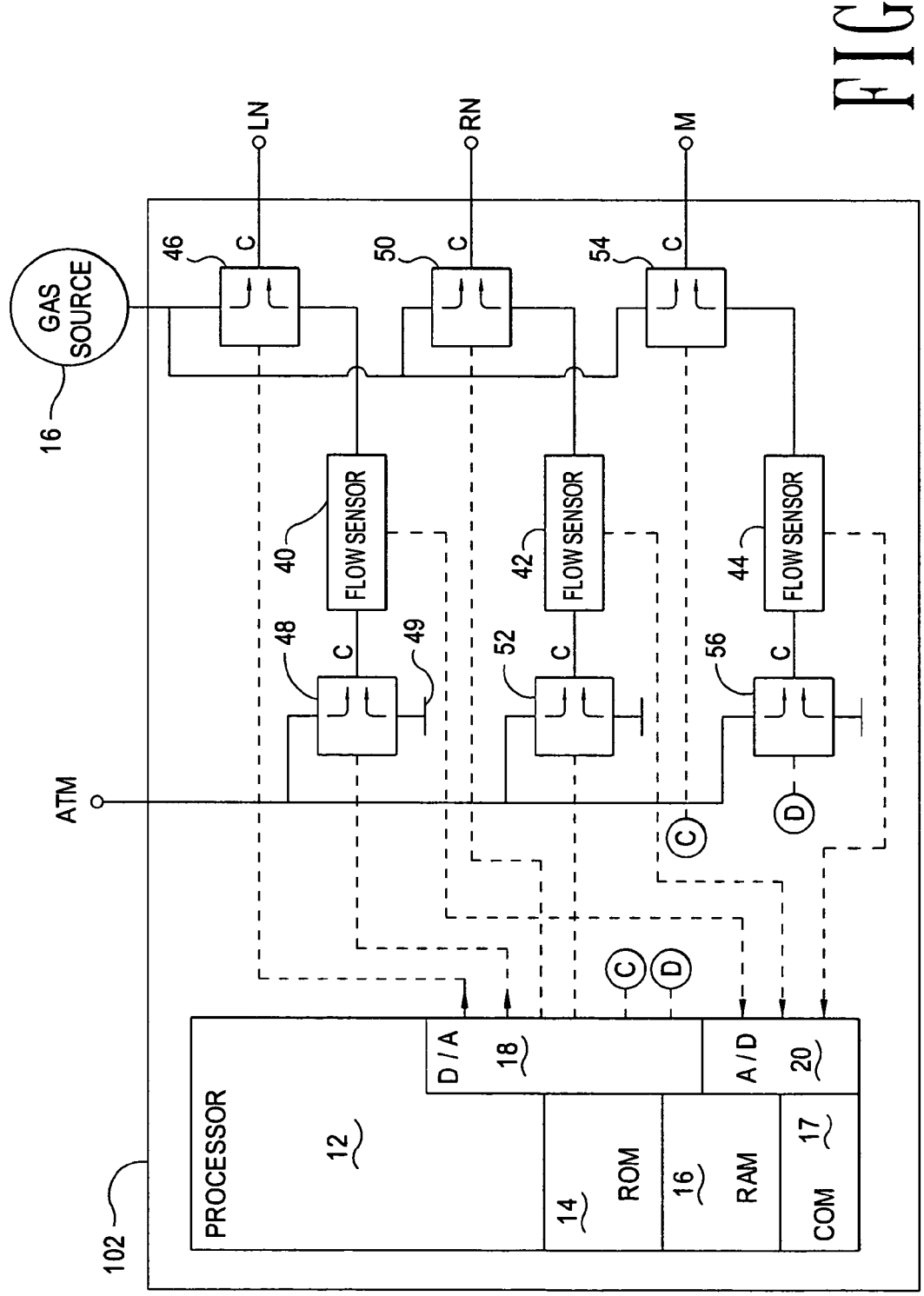
FIG. 3 illustrates a preferential delivery system in accordance with alternative embodiments of the invention.

FIG. 3 illustrates a preferential delivery system 102 constructed in accordance with alternative embodiments of the invention. Like the system of FIG. 1, the preferential delivery system 102 comprises a processor 12, possibly in the form of a microcontroller, comprising ROM 14, RAM 16, a D/A converter 18 and an A/D converter 20. Rather than pressure sensors, the preferential delivery system 102 may use flow sensors 40, 42 and 44. Thus, the preferential delivery system 102 may sense a portion of the flow associated with each breathing orifice. Consider for purposes of explanation the flow sensor 40 and three-port valves 46, 48 coupled to the left naris. Three-port valve 46, under command of the processor 12, may: couple the gas source 10 to the common port and therefore the exemplary left naris; and couple the flow sensor 40 to the common port and therefore the exemplary left naris. Thus, during a period of time when the preferential delivery system 102 provides therapeutic gas to the left naris (whether continuous or in a bolus form), the three-port valve 46 provides the therapeutic gas to the left naris and blocks the flow sensor. In a second valve position, the three-port valve 46 fluidly couples the flow sensor to the common port and therefore the exemplary left naris. However, and in accordance with embodiments of the invention, the flow sensor 40 may not be operational until gas can flow through the sensor. Three-port valve 48, in a first valve position, couples the flow sensor 40 to an atmospheric vent (marked ATM in the drawing), thus allow gas to flow through the flow sensor for measurement purposes. The three-port valve 48, in a second valve position, couples to a blocked port 49. Consider for purposes of explanation a preferential delivery system 102 operating in a conserve mode, where a bolus of gas is provided to one or more breathing orifices during inspiration. After a bolus has been delivered, the three-port valve 46 (and possibly the three-port valves 50 and 54) may change valve positions, thus fluidly coupling the flow sensor 40 to the common port and the exemplary left naris. If the flow sensor 40 outlet is not blocked, a portion of the therapeutic gas may reverse flow through the flow sensor 40 and out the atmospheric vent. Three-port valve 48 (as well as corresponding three-port valves 52 and 56) may be used to temporarily block reverse flow and loss of therapeutic gas, i.e. the valves may remain in a position that blocks flow for about 300 milliseconds after therapeutic gas delivery has stopped by a change of valve position by upstream three-port valves 46, 50 and 54. After the expiration of the period of time of possible reverse flow has ended, one or more of the three-port valves 48, 52 and 56 may change valve positions, thus allowing the flow sensors to sense airflow. The description with respect to the three-port valves 46, 48 and flow sensor 40 for the left naris is equally applicable for the corresponding structures for the right naris and mouth.

Figure 4A:
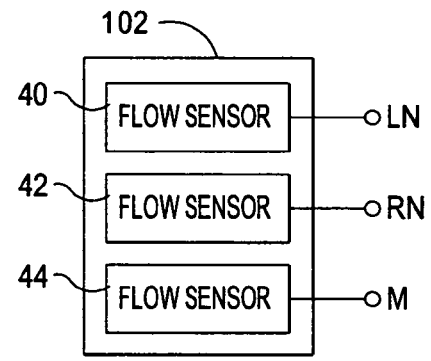
FIG. 4A illustrates, in shorthand notation, the system of FIG. 3.
Figure 4B:
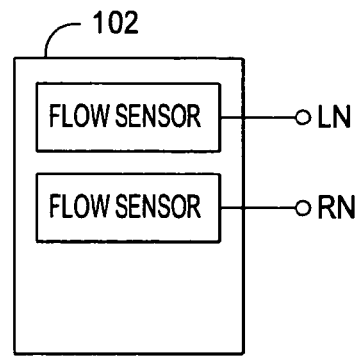
FIG. 4B illustrates an alternative embodiment of the system of FIG. 3.
Figure 4C:
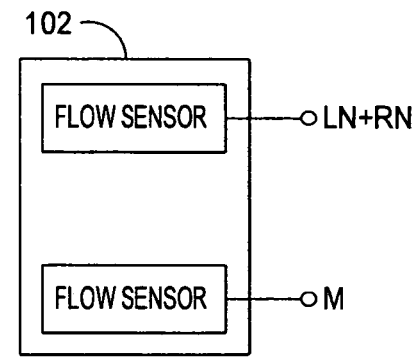
FIG. 4C illustrates yet another alternative embodiment of the system of FIG. 3.

FIG. 4A illustrates the preferential delivery system 102 of FIG. 3 in a shorthand notation, showing only flow sensors 40, 42 and 44 coupled to their respective breathing orifice. FIG. 4B illustrates alternative embodiments of the invention where only a patient's nares are used for sensing and delivery. In the embodiments of FIG. 4B, if both the left naris and the right naris are open to flow, the preferential delivery system 102 may deliver therapeutic gas to either naris, to both nares, or in an alternating fashion. In the event that either the left or right naris become clogged or blocked, or if the sensing and delivery tubing become dislodged, the preferential delivery system may provide therapeutic gas only to the unblocked naris. FIG. 4C illustrates further alternative embodiments where two flow sensors are used, but in this case only one flow sensor is associated with the nares, and the second flow sensor associated with the mouth. In the embodiments of FIG. 4C, a patient may utilize a single lumen cannula, and a second sensing and delivery tube associated with the mouth. The preferential delivery system 100 may thus selectively provide therapeutic gas to the nares and/or the mouth. In the event that either of the nares as a group or the mouth become blocked or otherwise unavailable for inspiration, the preferential delivery system 102 preferably provides therapeutic gas to the open breathing orifice.

Figure 5:
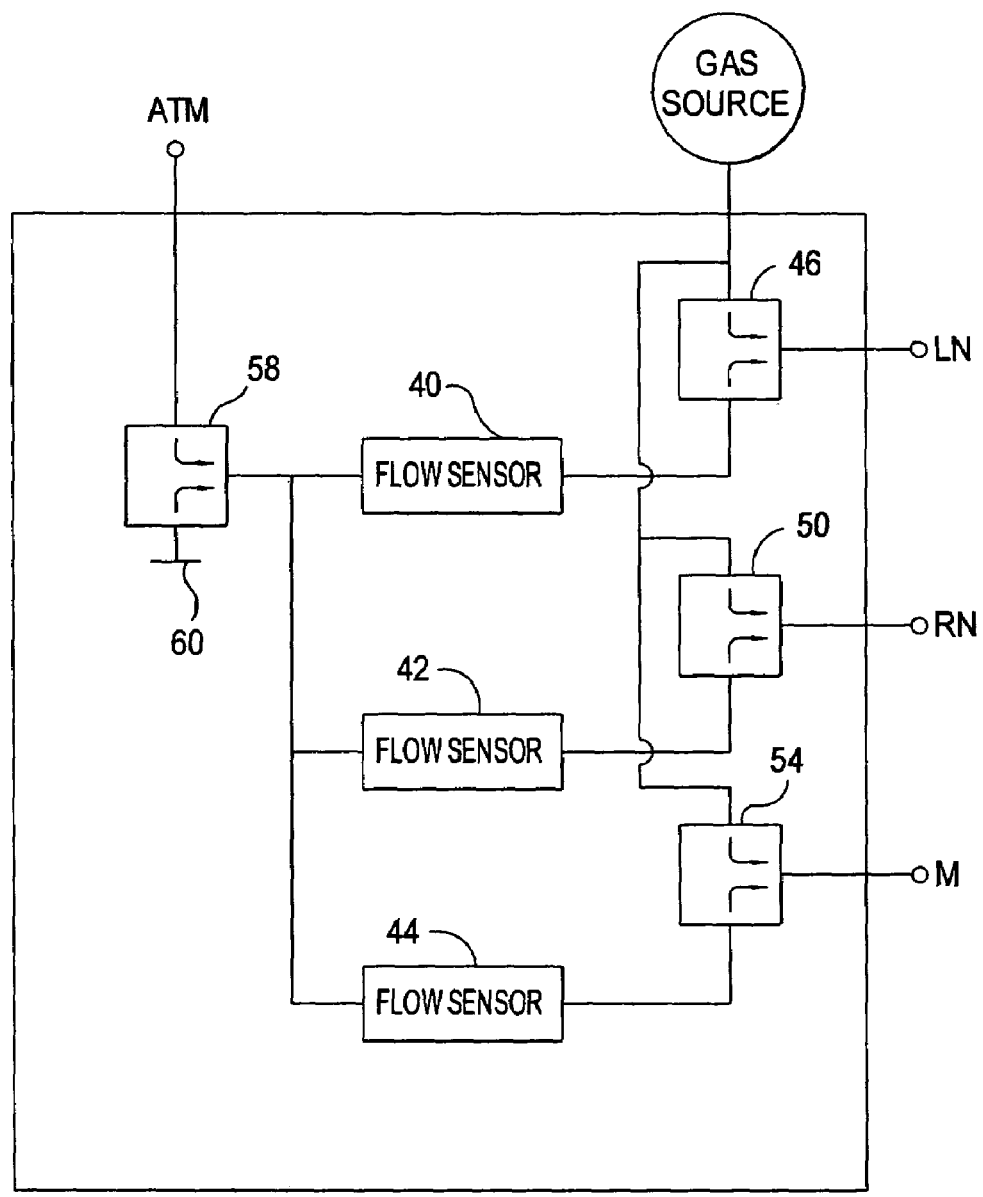
FIG. 5 illustrates an alternative embodiment of the system of FIG. 3 using fewer three-port valves.

FIG. 5 illustrates alternative embodiments of the invention utilizing flow sensors, but reducing the number of three-port valves used. The electrical components have been omitted from FIG. 5 for purposes of clarity. In particular, FIG. 5 illustrates that the three three-port valves 48, 52 and 56 of FIG. 3 may be replaced by a single three-port valve 58.

Blocking reverse flow through the flow sensors in the embodiments of FIG. 5 may be accomplished by single three-port valve 58. Relatedly, opening the second port of each of the flow sensors to the atmosphere vent so that flow may be detected may likewise be accomplished with a single three-port valve 58.

The embodiments discussed to this point control therapeutic gas flow in a boolean fashion. That is, therapeutic gas is either delivered to a breathing orifice, or the preferential delivery systems 100, 102 refrain from delivering therapeutic gas to a breathing orifice. However, alternative embodiments of the invention, which may be implemented using any of the exemplary embodiments described above, may control flow to each breathing orifice in proportion (either direct or inverse) to the amount of airflow drawn by that breathing orifice. Consider, for purposes of explanation, the pressure and flow sensor embodiments illustrated by FIGS. 2B and 4B. For a variety of reasons, such as congestion, physical abnormalities, periodic swelling of the nasal tissue, and the like, the amount of air flow drawn by a patient during inhalation through the nares may not be equal. By detecting a pressure and/or detecting a portion of the air flow through each naris, the preferential delivery systems 100, 102 may quantify the relationship between the air flow as between the nares. For example, the left naris of an exemplary patient may carry 20% of the airflow, and the right naris of a patient may carry the remaining 80% of the air flow. In the embodiments discussed above, therapeutic gas may only be delivered to the right naris, carrying the bulk of the airflow. In the alternative embodiments, the selective delivery systems 100, 102 may proportion delivery of therapeutic gas. In the example of an 20–80 split between the left naris and the right naris respectively, the preferential delivery system 100, 102 may correspondingly proportion therapeutic gas flow 20% to the left naris and 80% to the right naris, or vice-versa. As the patient's left naris becomes less congested (or the patient changes head position that affects air flow or swelling, the preferential delivery system may likewise change the proportion of therapeutic gas flow. Referring again to FIG. 3, proportioning therapeutic gas flow may be accomplished by pulse width modulating each of the three-port valves 46, 50 and 54 by the processor 12. In an exemplary situation where a patient's left naris carries only 20% of the total airflow and control is a direct proportion, the electrical signal from the processor 12 to the three-port valve 46 may be pulse width modulating at a duty cycle where only 20% of the therapeutic gas is delivered to the left naris. Although the discussion with respect to the alternative embodiments where therapeutic gas may be proportioned between breathing orifices focused only on proportioning the nares, the proportioning may likewise be done between the nares in general and the mouth, or all three breathing orifices.

In all of the embodiments, in the event an inhalation is not detected through any breathing orifice, an alarm may be sounded. Relatedly, if the preferential delivery systems sense an apnea event, an alarm may be sounded. Moreover, the patient's breathing patterns may be stored, such as in RAM 16, and communicated to external devices through communication port 17.

The above discussion is meant to be illustrative of the principles and various embodiments of the present invention. Numerous variations and modifications will become apparent to those skilled in the art once the above disclosure is fully appreciated. For example, while the use of a cannula, at least with respect to coupling the preferential delivery system to the nares, has been discussed, this is only exemplary and any system and method by which the therapeutic gas is fluidly coupled from the preferential delivery system to the breathing orifices of the patient may be equivalently used. A single lumen cannula may be operable in some situations with respect to the nares. Likewise, a bifurcated nasal cannula may be used with respect to the nares. Alternatively, a cannula may be used where the sensing lines couple to the flow sensors are separate and distinct from the lines in which therapeutic gas is delivered proximate to the breathing orifices. Further, while the various embodiments described use electrical components as the control system, other pneumatic/mechanical systems may be equivalently used. It is intended that the following claims be interpreted to embrace all such variations and modifications.

What is claimed is:

1. A method comprising:
   individually sensing airflow of each of a first and second breathing orifice of a patient; and
   delivering therapeutic gas to one of the first and second breathing orifice exhibiting greater airflow.

2. The method as defined in claim 1 wherein the first and second orifice are selected from the group comprising the left naris, right naris and mouth.

3. The method as defined in claim 1 wherein the sensing and delivery take place during the same inhalation.

4. The method as defined in claim 1 wherein the sensing and delivery take place during different inhalations.

5. The method as defined in claim 1 wherein delivering further comprises:
   delivering therapeutic gas to the first breathing orifice in an amount proportional to the airflow of the first orifice; and
   delivering therapeutic gas to the second orifice in an amount proportional to the airflow of the second orifice.

6. The method as defined in claim 5 wherein the delivering steps each further comprise delivering an amount directly proportional to airflow.

7. The method as defined in claim 1 further comprising:
   wherein sensing further comprises sensing airflow of a third breathing orifice of the patient; and
   wherein delivering further comprises delivering therapeutic gas to one of the first, second and third breathing orifice exhibiting greater airflow.

8. The method as defined in claim 7 wherein delivering further comprises delivering therapeutic gas to the first, second and third breathing orifices in an amount proportional to the airflow of the first, second and third breathing orifices respectively.

9. A system comprising:
   a control system;
   first and second sensors coupled to the control system;
   a first valve coupled to the control system and the first sensor, wherein in one valve position the first valve fluidly couples a source of therapeutic gas to a common port of the first valve, and in a second valve position the first valve fluidly couples the first sensor to the common port of the first valve, and wherein the common port of the first valve configured to fluidly couple to a first breathing orifice of a patient;
   a second valve coupled to the control system and the second sensor, wherein in one valve position the second valve fluidly couples a source of therapeutic gas to a common port of the second valve, and in a second valve position the second valve fluidly couples the second sensor to the common port of the second valve, and wherein the common port of the second valve configured to fluidly couple to a second breathing orifice of the patient; and wherein the control system determines a first and second sensed parameter indicative of airflow of the first and second breathing orifices using the first and second sensors, wherein the control system commands the first valve to supply therapeutic gas to the common port of the first valve only if the first sensed parameter indicates the presence of airflow, and wherein the control system commands the second valve to supply therapeutic gas to the common port of the second valve only if the first sensed parameter indicates the presence of airflow.

10. The system as defined in claim 9 wherein the control system determines the first sensed parameter and commands the first valve to supply therapeutic gas in the same inspiration of the patient.

11. The system as defined in claim 9 wherein the control system determines the first sensed parameter and commands the first valve to supply therapeutic gas in different inspirations of the patient.

12. The system as defined in claim 9 further comprising wherein the first sensor is a pressure sensor, and wherein the first sensed parameter is a pressure indicative of airflow.

13. The system as defined in claim 9 further comprising wherein the first sensor is a flow sensor, and wherein the first sensed parameter is at least a portion of the airflow of the first breathing orifice.

14. The system as defined in claim 9 wherein the control system commands the first valve to provide therapeutic gas flow in proportion to the first sensed parameter.

15. The system as defined in claim 14 wherein the control system commands the first valve to provide therapeutic gas flow in direct proportion to the first sensed parameter.

16. The system as defined in claim 9 further comprising:
wherein the control system further comprises a processor;
wherein the first sensor further comprises an output signal line coupled to the processor; and
wherein the first valve further comprises a control input signal coupled to the processor, and wherein the processor commands the valve by way of the control input signal line.

17. A method comprising:
sensing airflow of a patient's first and second naris individually;
delivering therapeutic gas to the first naris in proportion to the airflow of the first naris; and
delivering therapeutic gas to the second naris in proportion to the airflow of the second naris.

18. The method as defined in claim 17 wherein delivering further comprises delivering to a naris only if the naris is open to airflow.

19. The method as defined in claim 17 wherein the sensing and delivering steps take place during the same inspiration.

20. The method as defined in claim 17 wherein the sensing and delivering steps take place during different inspirations.

21. The method as defined in claim 17 wherein sensing further comprises:
sensing a pressure indicative of airflow of the first naris; and
sensing a pressure indicative of airflow of the second naris.

22. The method as defined in claim 17 wherein sensing further comprises:
sensing at least a portion of the airflow of the first naris; and
sensing at least a portion of the airflow of the second naris.

23. The method as defined in claim 17 wherein the delivering steps further comprise delivering therapeutic gas in direct proportion to airflow.

24. The method as defined in claim 17 further comprising:
storing data regarding airflow of the patient's nares; and
delivering the data external requestors.

25. A therapeutic gas delivery system comprising:
a gas port adapted to coupled to a source of therapeutic gas;
a first narial port adapted to couple to a first naris of a patient;
a second narial port adapted to couple to a second naris of the patient; and
wherein the therapeutic gas delivery system fluidly couples the gas port to the first narial port if airflow through the first naris is sensed, and wherein the therapeutic gas deliver system further fluidly couples the gas port to the second narial port if airflow through the second naris is sensed.

26. The therapeutic gas delivery system as defined in claim 25 wherein the therapeutic gas delivery system couples the gas port to the first and second narial ports for delivery of therapeutic gas in continuous fashion, and periodically decouples the gas port from one or both of the first and second narial port to sense airflow.

27. The therapeutic gas delivery system as defined in claim 25 wherein the therapeutic gas delivery system senses airflow during an inhalation of the patient, and fluidly couples the gas port to the first narial port if airflow is sensed through the first naris during the inhalation, and further fluidly couples the gas port to the second narial port if airflow is sensed through the second naris during the inhalation.

28. The therapeutic gas delivery system as defined in claim 25 further configured to fluidly couple the gas port to the first narial port and provide a therapeutic gas flow proportional to the airflow through the first naris, and configured to fluidly couple the gas port to the second narial port and provide a therapeutic gas flow proportional to airflow through the second naris.

29. The therapeutic gas delivery system as defined in claim 28 further configured to fluidly couple the gas port to the first narial port and provide a therapeutic gas flow in direct proportion to the airflow through the first naris, and configured to fluidly couple the gas port to the second narial port and provide a therapeutic gas flow in direct proportion to airflow through the second naris.

30. The therapeutic gas delivery system as defined in claim 25 further comprising:
an oral port adapted to couple to the mouth of the patient; and
wherein the therapeutic gas delivery system fluidly couples the gas port to the oral port if airflow is sensed through the mouth of the patient.

31. The therapeutic gas delivery system as defined in claim 30 wherein if airflow is sensed in each of the first naris, the second naris and the mouth, the therapeutic gas delivery system is configured to couple the gas port to the first narial port, the second narial port and the oral port in a rotating fashion.

32. A method comprising:
measuring airflow of a first naris of a patient, and providing therapeutic gas to the first naris based on the measuring; and measuring airflow of a second naris of the patient, and providing therapeutic gas to the second naris based on the measuring of the second naris.

33. The method as defined in claim 32 wherein the providing steps further comprise providing a bolus of therapeutic gas, and wherein the volume of the bolus is divided between the first and second naris based on the results of their respective measuring steps.

34. The method as defined in claim 32 wherein the providing steps further comprise providing therapeutic gas at a total flow rate, and wherein the total flow rate is the sum of a flow rate provided to the first naris and a flow rate provided to the second naris based on their respective measuring steps.

35. A therapeutic gas delivery system comprising:
a first sensor and first valve coupled to a first narial port, the first narial port configured to couple to a first naris of a patient;
a second sensor and second valve coupled to a second narial port, the second narial port configured to couple to a second naris of the patient; and
wherein the first sensor senses airflow of the first naris with the first valve in one position, and with the first valve in another position the first valve couples therapeutic gas to the first narial port;
wherein the second sensor senses airflow of the second naris with the second valve in one position, and with the second valve in another position the second valve couples therapeutic gas to the second narial port;
wherein the therapeutic gas delivery system only delivers therapeutic gas to the first naris if airflow is sensed in the first naris, and only delivers therapeutic gas to the second naris if airflow is sensed in the second naris.

36. The therapeutic gas delivery system as defined in claim 35 wherein, if airflow is sensed in both the first and second naris, the therapeutic gas delivery system alternates delivery of therapeutic gas to the first and second narial ports.

37. The therapeutic gas delivery system as defined in claim 35 further comprising:
said first valve configured to control a volume of therapeutic gas coupled to the first narial port, the volume based on the airflow of the first naris; and
said second valve configured to control a volume of therapeutic gas coupled to the second narial port, the volume based on the airflow of the second naris.

38. The therapeutic gas delivery system as defined in claim 37 wherein a total volume delivered to the combined first and second narial ports is controlled.

39. The therapeutic gas delivery system as defined in claim 35 wherein the first and second valves couple therapeutic gas to their respective nares for continuous mode operation, and periodically couple the first and second sensors to sense airflow.

40. A system comprising:
a processor;
a first sensor having an output signal line coupled to the processor;
a second sensor having an output signal line coupled to the processor;
a first valve having a control input signal line coupled to the processor, wherein in one valve position the first valve fluidly couples a source of therapeutic gas to a common port of the first valve, and in a second valve position the first valve fluidly couples the first sensor to the common port of the first valve, and wherein the common port of the first valve configured to fluidly couple to a first breathing orifice of a patient;
a second valve having a control input signal line coupled to the processor, wherein in one valve position the second valve fluidly couples a source of therapeutic gas to a common port of the second valve, and in a second valve position the second valve fluidly couples the second sensor to the common port of the second valve, and wherein the common port of the second valve configured to fluidly couple to a second breathing orifice of the patient; and
wherein the processor is programmed to read the output signal lines of the first and second sensors to determine a first and second values indicative of airflow of the first and second breathing orifices respectively, wherein the processor is further programmed to assert the control input signal line to the first valve to supply therapeutic gas to the common port of the first valve only if the first value indicates the presence of airflow, and wherein the processor is further programmed to assert the control input signal line to the second valve to supply therapeutic gas to the common port of the second valve only if the second value indicates the presence of airflow.

41. The system as defined in claim 40 further comprising wherein the processor reads the output signal line of the first sensor and asserts the control input signal line of the first valve to supply therapeutic gas in the same inspiration of the patient.

42. The system as defined in claim 40 further comprising wherein the processor reads the output signal line of the first sensor and asserts the control input signal line of the first valve to supply therapeutic gas in the same different inspirations of the patient.

43. The system as defined in claim 40 further comprising wherein the first sensor is a pressure sensor, and wherein the first value is a pressure indicative of airflow.

44. The system as defined in claim 40 further comprising wherein the first sensor is a flow sensor, and wherein the first value is a value representing at least a portion of the airflow of the breathing orifice.

45. The system as defined in claim 40 wherein the processor pulse-width modulates the control input signal lines to provide therapeutic gas flow in proportion to the first and second values.

46. The system as defined in claim 45 wherein the processor pulse-width modulates the control input signal lines to provide therapeutic gas flow in direct proportion to the first and second values.

* * * * *